US008994945B2

(12) United States Patent
Duplisea et al.

(10) Patent No.: US 8,994,945 B2
(45) Date of Patent: Mar. 31, 2015

(54) METHOD OF TREATMENT ANALYSIS WITH PARTICLE IMAGING

(71) Applicant: Fluid Imaging Technologies, Inc., Yarmouth, ME (US)

(72) Inventors: Matthew Duplisea, Gorham, ME (US); Corie Drake, Portland, ME (US); Mason Ide, Gorham, ME (US)

(73) Assignee: Fluid Imaging Technologies, Inc., Scarborough, ME (US)

( * ) Notice: Subject to any disclaimer, the term of this patent is extended or adjusted under 35 U.S.C. 154(b) by 8 days.

(21) Appl. No.: 13/662,156

(22) Filed: Oct. 26, 2012

(65) Prior Publication Data

US 2013/0107261 A1    May 2, 2013

Related U.S. Application Data

(60) Provisional application No. 61/552,032, filed on Oct. 27, 2011.

(51) Int. Cl.
*G01J 3/46* (2006.01)
*G01N 21/27* (2006.01)
*G01N 15/14* (2006.01)

(52) U.S. Cl.
CPC ........ *G01N 21/27* (2013.01); *G01N 2015/1465* (2013.01); *G01N 2015/1493* (2013.01); *G01N 2015/1497* (2013.01); *G01N 15/1463* (2013.01)
USPC .......................................................... 356/402

(58) Field of Classification Search
USPC .............................. 356/402–425
See application file for complete search history.

(56) References Cited

U.S. PATENT DOCUMENTS

| | | |
|---|---|---|
| 4,407,008 A | 9/1983 | Schmidt et al. |
| 4,412,246 A | 10/1983 | Allen et al. |
| 4,612,614 A | 9/1986 | Deindoerfer et al. |
| 4,673,288 A | 6/1987 | Thomas et al. |
| 4,778,593 A | 10/1988 | Yamashita |
| 4,818,103 A | 4/1989 | Thomas et al. |
| 4,902,137 A | 2/1990 | Krieg et al. |
| 5,017,497 A | 5/1991 | de Grooth et al. |
| 5,087,823 A | 2/1992 | Silvy et al. |
| 5,117,466 A | 5/1992 | Buican |
| 5,159,397 A | 10/1992 | Kosaka et al. |

(Continued)

FOREIGN PATENT DOCUMENTS

JP      2000338030      12/2000

OTHER PUBLICATIONS

Notification of International Search Report and Written Opinion in PCT application No. PCT/US09/02562, dated Jul. 17, 2009, 7 pp.

(Continued)

*Primary Examiner* — Abdullahi Nur
(74) *Attorney, Agent, or Firm* — Caseiro Burke LLC; Chris A. Caseiro (57) ABSTRACT

A method for determining the effectiveness of the treatment of a fluid for the purpose of reducing or eliminating particles in the fluid. The method includes the steps of obtaining samples of the fluid before and after treatment, delivering the samples to a particle imaging system, obtaining image information of particles in the samples, including particle colors, and comparing the difference in particle color from the first sample to the second sample. A change in particle color detected is indicative of particle death.

5 Claims, 6 Drawing Sheets

(56) References Cited

U.S. PATENT DOCUMENTS

| | | | |
|---|---|---|---|
| 5,159,398 | A | 10/1992 | Maekawa et al. |
| 5,247,339 | A | 9/1993 | Ogino |
| 5,247,340 | A | 9/1993 | Ogino |
| 5,248,451 | A | 9/1993 | Tsunaga et al. |
| 5,311,290 | A | 5/1994 | Olson et al. |
| 5,448,349 | A | 9/1995 | Kosaka |
| 5,471,294 | A | 11/1995 | Ogino |
| 5,650,610 | A | 7/1997 | Gagnon |
| 5,824,269 | A | 10/1998 | Kosaka et al. |
| 5,850,284 | A | 12/1998 | Schoeffler et al. |
| 5,852,498 | A | 12/1998 | Youvan et al. |
| 6,028,663 | A | 2/2000 | O'Mongain et al. |
| 6,067,155 | A | 5/2000 | Ringlien |
| 6,115,119 | A | 9/2000 | Sieracki et al. |
| 6,525,875 | B1 | 2/2003 | Lauer |
| 6,674,058 | B1 | 1/2004 | Miller |
| 7,030,981 | B2 | 4/2006 | Bishop et al. |
| 7,271,897 | B2 | 9/2007 | Wolleschensky |
| 7,312,919 | B2 | 12/2007 | Overbeck |
| 7,532,326 | B2 | 5/2009 | Corcoran |
| 7,576,862 | B2 | 8/2009 | Cromwell |
| 7,599,545 | B2 | 10/2009 | Shibata et al. |
| 7,796,256 | B2 | 9/2010 | Sieracki et al. |
| 8,005,314 | B2 | 8/2011 | Ortyn et al. |
| 2005/0030373 | A1 | 2/2005 | Chao et al. |
| 2006/0177937 | A1 | 8/2006 | Kurabayashi et al. |
| 2006/0197032 | A9 | 9/2006 | Oostman, Jr. et al. |
| 2007/0139541 | A1 | 6/2007 | Fein et al. |
| 2007/0184471 | A1 | 8/2007 | Yguerabide et al. |
| 2009/0125242 | A1 | 5/2009 | Choi et al. |
| 2009/0174703 | A1* | 7/2009 | Hermanson et al. .......... 345/419 |
| 2009/0273774 | A1 | 11/2009 | Sieracki et al. |
| 2009/0283697 | A1 | 11/2009 | Sieracki et al. |
| 2012/0002029 | A1 | 1/2012 | Sieracki et al. |
| 2012/0127298 | A1 | 5/2012 | Sieracki et al. |

OTHER PUBLICATIONS

Oldenbourg, R., Methods in Molecular Medicine: Analysis of Microtubule Dynamics of Polarized Light, Methods Mol. Med. 2007, 137, 111-123, US.

Johnson, L., Enhanced early detection and enumeration of zebra mussel (*Drieissna* spp.) veligers using cross-polarized light microscopy, Hydrobiologica, 1995, 312, Belgium.

Marie, D. et al., Enumeration of Marine Viruses in Culture and Natural Samples by Flow Cytometry, Applied and Environmental Microbiology, Jan. 1999, vol. 65, No. 1; 45-52, US.

Website page mccroneassociates.com/Techniques/detailasp?TECHNIQUES_ID=19& of McCrone Associates, 1 pp.

Statement regarding common ownership of patent documents describing related technology, Oct. 31, 2012, 2 pp.

Kay, DB et al., Imaging in Flow, Journal of Histochemistry and Cytochemistry, vol. 27, No. 1, pp. 329-334, 1979.

* cited by examiner

METHOD OF TREATMENT ANALYSIS WITH PARTICLE IMAGING

CROSS REFERENCE TO RELATED APPLICATION

The present application is a nonprovisional and claims the priority benefit of U.S. provisional patent application Ser. No. 61/552,032 filed Oct. 27, 2011, entitled METHOD OF TREATMENT ANALYSIS WITH FLOW CYTOMETER by the same named inventors and held by a common assignee. The entire content of that priority application is incorporated herein by reference.

BACKGROUND OF THE INVENTION

1. Field of the Invention

The present invention relates generally to an optical flow imaging and analysis configuration used in particle analysis instrumentation, and more particularly to an optical flow imaging system used to detect the effectiveness of fluid treatment.

2. Description of the Prior Art

The art has seen various optical/flow systems employed for transporting a fluid within an analytical instrument to an imaging and optical analysis area. A liquid sample is typically delivered into the bore of a flow chamber and this sample is interrogated in some way so as to generate analytical information concerning the nature or properties of the sample. For example, a laser beam may excite the sample that is present in the bore of the capillary, with the emitted fluorescence energy representing the signal information.

From an optical perspective, the objectives and flow chambers have included those of low to medium numerical aperture (NA). A typical flow imaging system includes a cylindrical or rectangular glass rod having a hollow co-axial cylindrical or rectangular bore of smaller diameter, in which the sample to be analyzed is placed. With the sample in place, optical analysis is performed with low to medium numerical aperture (NA) optics (e.g., NA 32 0.6), typically an air objective. Such low to medium NA optics are considered easier to use and more suitable for dealing with the limitation of having the fluid of interest spaced from the optics by the thickness of the rod wall, which are simply too thick to permit use of high NA optics.

Nevertheless, high NA optics systems have been developed and used to detect the content of fluid samples. One such system that has proven to be effective at organism detection is described in U.S. Pat. No. 7,796,256, issued Sep. 14, 2010. That system includes an oil-immersion arrangement to facilitate the use of high NA optics. The entire content of U.S. Pat. No. 7,796,256 is incorporated herein by reference.

The flow-based imaging systems in existence to date have been limited in their usage as an aid to determine the quantity and type of organism contained in a fluid sample. That information is of value in understanding what is likely in the fluid from which that sample was acquired. The recipient of that information must then decide what to do, if anything, with that knowledge. Until the present invention, imaging systems were employed only to establish organism type and, as effectively as possible, the number of such organisms per some volumetric value. Beyond that, imaging systems, including flow cytometers, have not been used for the purpose of assessing the effectiveness of any effort carried out to deal with such organisms. Primarily, the organism or organisms for which neutralization or elimination is of interest.

To date, imaging systems have not been used for the purpose of assessing the effectiveness of efforts to neutralize or eliminate organisms of a fluid. For example, undesirable organisms contained in drinking water and ballast water, but not limited thereto. What is needed is a system and method for determining the effectiveness of fluid treatment efforts.

SUMMARY OF THE INVENTION

The present invention is a method for using flow-based particle imaging to determine the effectiveness of a fluid treatment effort. The method includes the use of an optical system including a flow chamber, an imaging objective, and an imaging light source, as well as an objective and a condenser. Any form of such a system may be employed, provided it generates sufficient resolution to ensure the detection of organisms in a manner that allows the user to distinguish the difference between live organisms and dead ones. Suitable forms of the system include, without limitation, the FlowCam® imaging system provided by Fluid Imaging Technologies, Inc., of Yarmouth, Me. A flow cytometer may be used.

The method of the present invention includes as primary steps the steps of acquiring one or more samples from a fluid prior to treatment, passing the sample or samples through the flow-based particle imaging system, gathering data regarding characteristics of particles, such as organisms, in the sample (s) and storing that data. The method further includes the steps of acquiring another one or more samples from the fluid after treatment, passing the sample or samples through the imaging system, gathering data regarding characteristics of the particles in the sample(s) and storing that data. The steps associated with acquiring one or more samples of the fluid after treatment, passing the sample(s) through the imaging system and gathering data of particle characteristics may be repeated one or more times. The characteristics information gathered, including colors of the organisms, before and after treatment of the fluid are then compared to observe any changes in those characteristics that may have occurred as a result of the fluid treatment effort. The inventors of the present invention have determined that organisms presenting a first color when alive present a second, different, color when dead. More specifically, the second color has been determined to be evidence of the death of the organism wherein the remains of the organism become transparent. In experiments conducted, it was observed that some organisms that had died presented a blue color in the imaging analysis as an indication of their transparency. Other organisms present other colors after death, including green and red, for example, and even those that change from opaque to transparent represent organism death.

The method of the present invention enables the evaluation of the effectiveness of a fluid treatment procedure to eliminate particles, such as organisms, from the fluid. When a fluid, such as the water of a watercraft ballast tank, is treated with a cleaning solution, such as chlorine, there is a desire to determine whether sufficient harmful organisms have been destroyed. The method of the present invention allows for that determination by enabling the examination of those organisms before and after the treatment.

This and other advantages of the present invention will become more readily apparent upon review of the following detailed description, the accompanying drawings and the appended claims.

DETAILED DESCRIPTION OF THE PREFERRED EMBODIMENT

Figure 1:
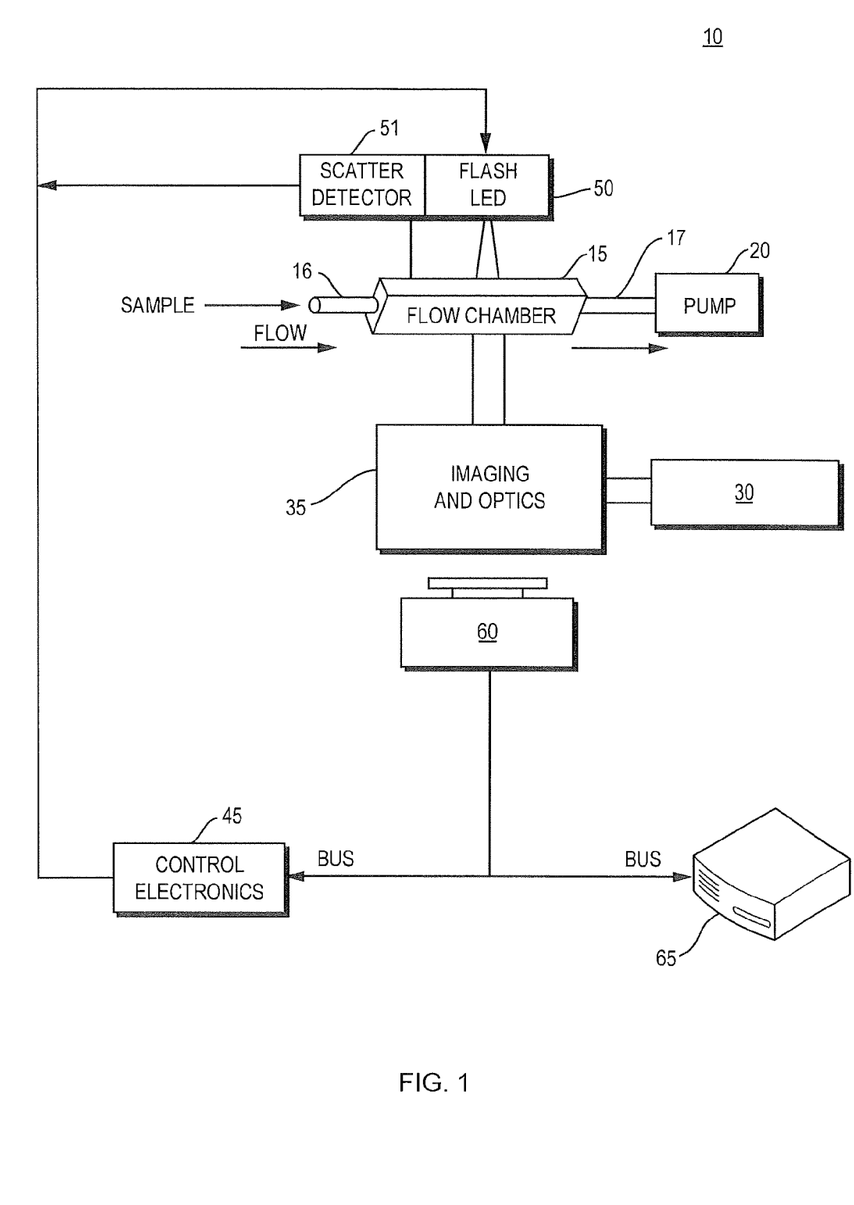
FIG. 1 schematically illustrates a system for studying particles in a fluid according to one embodiment of the invention.
Figure 2:
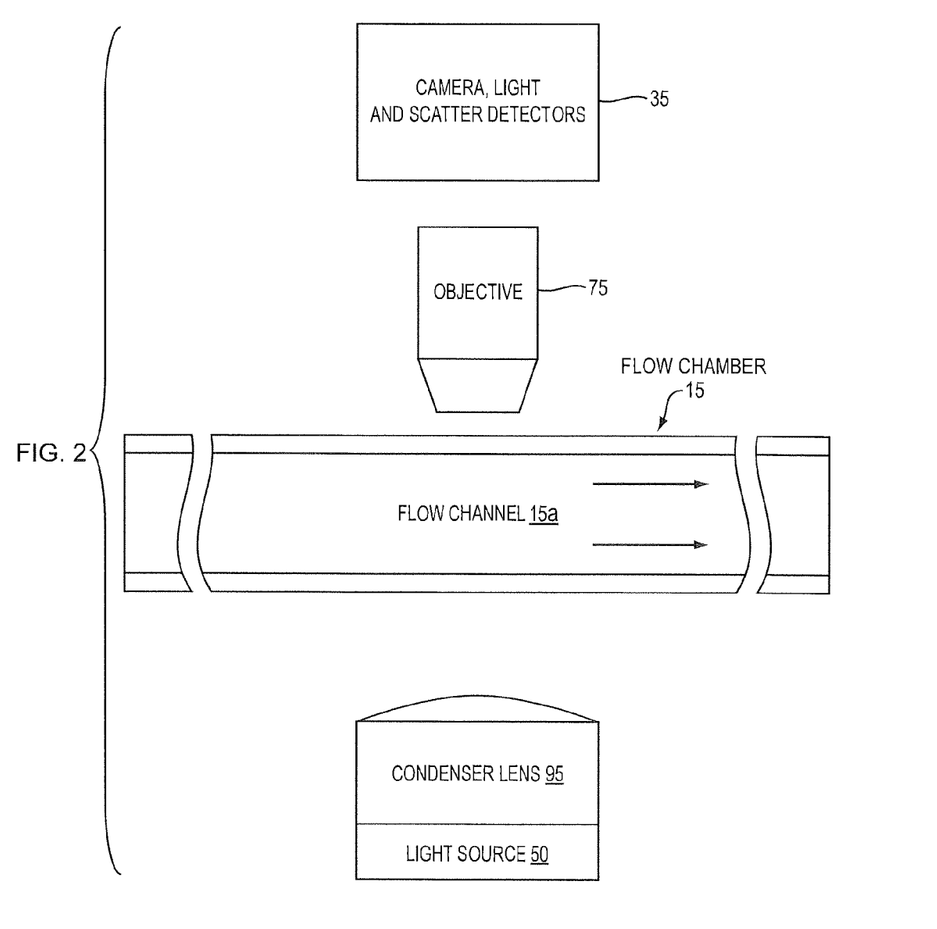
FIG. 2 is an enlarged perspective view of the optics and flow chamber of the system of FIG. 1.

A system 10 suitable for use in carrying out the method of the present invention in high quality imaging that exist in a fluid sample is shown in FIGS. 1 and 2. The system 10 includes a flow chamber 15, a light source 30, optics 35, an image detection system 40, a backlighting generator 50, an image capturing system 60, a computing device 65, a high NA objective 75 and a high NA condenser lens 95. The combination of these components of the system 10 arranged and configured as described herein enable a user to detect particles in the fluid and produce high resolution images of those particles. The system 10 illustrated is a presentation of one form of the FlowCam® flow-based particle imaging system available from Fluid Imaging Technologies, Inc., of Yarmouth, Me. A flow cytometer may be used for that purpose.

The flow chamber 15 includes an inlet 20 for receiving the particle-containing fluid to be observed, and an outlet 25 through which the fluid passes out of the flow chamber 15 after imaging functions have been performed. The flow chamber 15 may be fabricated of a material that does not readily fluoresce, including, for example, but not limited to, microscope glass or rectangular glass extrusions, or other materials suitable to allow particle detection and imaging. The flow chamber 15 may be circular or rectangular in shape. The flow chamber 15 defines a channel 15a through which the fluid flows at a predetermined selectable rate. The channel 15a may be of rectangular configuration. The flow chamber 15 is fabricated with a wall thickness that substantially matches the thickness considered suitable by the manufacturer of the high NA objective 75 described herein. For example, the wall thickness of the flow chamber 15 should substantially match that of a microscope cover slide. The inlet 20 of the flow chamber 15 is connectable to a fluid source and the outlet 25 is connectable to a downstream means for transferring the fluid away from the flow chamber 15.

A light source 30 is used to generate excitation light, which is passed through the optics 35 to the flow chamber 15, resulting in particle light scatter. The light source 30 may be a Light Emitting Diode (LED) or another form of light source. The detection system 40, which may include a lens, is configured to detect particles existing in the flow chamber 15 when the light source 30 is activated. Output from the detection system 40 is processed by detection electronics 45. Preferably, the detection electronics 45 includes user-adjusted gain and threshold settings which determine the amount of scatter required for the system 10 to acknowledge a passing particle. The detection electronics 45 may be configured to receive input signals and produce output information compatible with the specific needs of the user of the system 10. An example of a suitable electronics system capable of performing the signal activation and output information associated with the detection electronics 45 of the system 10 is the detection electronics described in U.S. Pat. No. 6,115,119 issued Sep. 5, 2000, the entire content of which is incorporated herein by reference. Those of ordinary skill in the art will recognize that the specific electronics system described therein may be modified, such as through suitable programming for example, to trigger desired signal activation and/or to manipulate received signals for desired output information.

If a sufficiently lighted particle passes through the flow chamber 15, a signal from the detection system 40 is sent to the detection electronics 45, which then generate one or more trigger signals that are transmitted to the computing device 65. The computing device 65 is programmed to store the information received from the detection electronics 45 and to make calculations associated with the particles detected. For example, but not limited thereto, the computing device 65 may be programmed to provide specific information regarding the shape of the particles, dimensions of the particles, and specific features of the particles. The computing device 65 may be any sort of computing system suitable for receiving information, running software programs on its one or more processors, and producing output of information, including, but not limited to images and data, that may be observed on a user interface.

The detection electronics 45 may also be coupled, directly or indirectly through the computing device 65 to the backlighting generator 50. In particular, the detection electronics 45 and/or the computing device 65 may include an arrangement whereby a user of the system 10 may alternatively select a setting to automatically generate a trigger signal at a selectable time interval. The trigger signal generated produces a signal to activate the operation of the backlighting generator 50 so that a light flash is generated. Specifically, the backlighting generator 50 may be a LED or other suitable light generating means that produces a light of sufficient intensity to backlight the flow chamber 15 and image the passing particles. The very high intensity LED flash may be a "white" LED flash, or a flash of another other suitable wavelength, which is flashed on one side of the flow chamber 15 for 200 μsec (or less). At the same time, the image capturing system 60 positioned on the opposing side of the flow chamber 15 is activated to capture an instantaneous image of the particles in the fluid as "frozen" when the high intensity flash occurs. The image capturing system 60 is arranged to either retain the captured image, transfer it to the computing device 65, or a combination of the two. The image capturing system 60 includes characteristics of a digital camera or an analog camera with a framegrabber or other means for retaining images. For example, but in no way limiting what this particular component of the system may be, the image capturing system 60 may be, but is not limited to being, a CCD firewire, a CCD USB-based camera, or other suitable device that can be used to capture images and that further preferably includes computing means or that may be coupled to computing means for the purpose of retaining images and to manipulate those images as desired. The computing device 65 may be programmed to measure the size and shape of the particle captured by the image capturing system 60 and/or store the data for later analysis.

The system 10 also includes the high NA objective 75 and the high NA condenser lens 95 as part of the optics 35. The high NA condenser lens 95 aids in clear illumination of that section of the fluid in the flow channel 15a that is to be imaged by focusing the high intensity flash from the backlighting generator 50 to that section. The high NA condenser lens 95 includes characteristics of a numerical aperture of about 1.25 and may be the AA2354932 1.25NA Abbe condenser available from Motic Incorporation Ltd. of Hong Kong. The high NA objective 75 is arranged to focus the illuminated image to the image capturing system 60. The high NA objective 75 also focuses fluorescence excitation light from the light source 30 onto the flow chamber 15. Further, the high NA objective 75 focuses the resulting scattered light onto the detection system 40. The high NA objective 75 is selected to have a range of focus or "working distance" which ensures that focus is substantially maintained through the entirely of the cross section of the flow channel 15a. Further, the high NA objective 75 includes characteristics of a numerical aperture greater than 0.7 and may be the EF Plan 100X/1.25NA available from Motic Incorporation Ltd. of Hong Kong.

The method of the present invention embodied in one or more computer programs includes steps associated with storing and analyzing images captured with the system 10 of the present invention. In the first step, the light source 30 and imaging optics 35 generate scatter excitation light, which is directed to the flow chamber 15 within which a fluid to be monitored passes. The detection system 40 including the control electronics 45 is used to detect separately, images associated with the light waveforms scattered from particles in the flow chamber 15. The detected images are transferred to the computing device 65 for storage and analysis. The images captured are characterized based on particle shape, size and color, in addition to other information that may be of interest. Color features representative of the particles in the fluid are detected and reported in a visual manner. For example, the information may be presented in graphic representations, spreadsheet lists, or combinations thereof. Optionally, the acquired image information may be used to count the number of particles in the fluid sample observed and reported. Captured images are compared to known or similar images of particles of interest and reported.

The steps identified are carried out in the examination of a fluid source, wherein fluid samples are acquired from the fluid source and transferred to the flow chamber 15. The fluid samples are acquired before and after treatment of the fluid source. For example, if the fluid source is a ballast tank, one or more first samples are acquired and examined. A treatment procedure is then completed and a second examination is performed by taking one or more new samples from the fluid source that has been treated. The examination steps may be repeated before and after treatment as desired.

It is to be understood that the computing device 65 used to gather the captured image information and to perform calculations and observe features of the captured image information may be associated with local or remote computing means, such as one or more central computers, in a local area network, a metropolitan area network, a wide area network, or through intranet and internet connections. The computing device 65 may include one or more discrete computer processor devices. The computing device may include computer devices operated by a centralized administrative entity or by a plurality of users located at one or more locations.

The computing device 65 may be programmed to include one or more of the functions of the system 10. The computing device 65 may include one or more databases including information related to the use of the system 10. For example, such a database may include known images of example particles of interest. The database may be populated and updated with information provided by the user and others.

The steps of the method described herein may be carried out as electronic functions performed through the computing device 65 based on computer programming steps. The functions configured to perform the steps described herein may be implemented in hardware and/or software. For example, particular software, firmware, or microcode functions executing on the computing device 65 can provide the trigger, image capturing and image analysis functions. Alternatively, or in addition, hardware modules, such as programmable arrays, can be used in the devices to provide some or all of those functions, provided they are programmed to perform the steps described.

The steps of the method of the present invention, individually or in combination, may be implemented as a computer program product tangibly as computer-readable signals on a computer-readable medium, for example, a non-volatile recording medium, an integrated circuit memory element, or a combination thereof. Such computer program product may include computer-readable signals tangibly embodied on the computer-readable medium, where such signals define instructions, for example, as part of one or more programs that, as a result of being executed by a computer, instruct the computer to perform one or more processes or acts described herein, and/or various examples, variations and combinations thereof. Such instructions may be written in any of a plurality of programming languages known to those of skill in the art including, for example, C++, but not limited thereto. The computer-readable medium on which such instructions are stored may reside on one or more of the components of system 10 described above and may be distributed across one or more such components.

Figure 3:
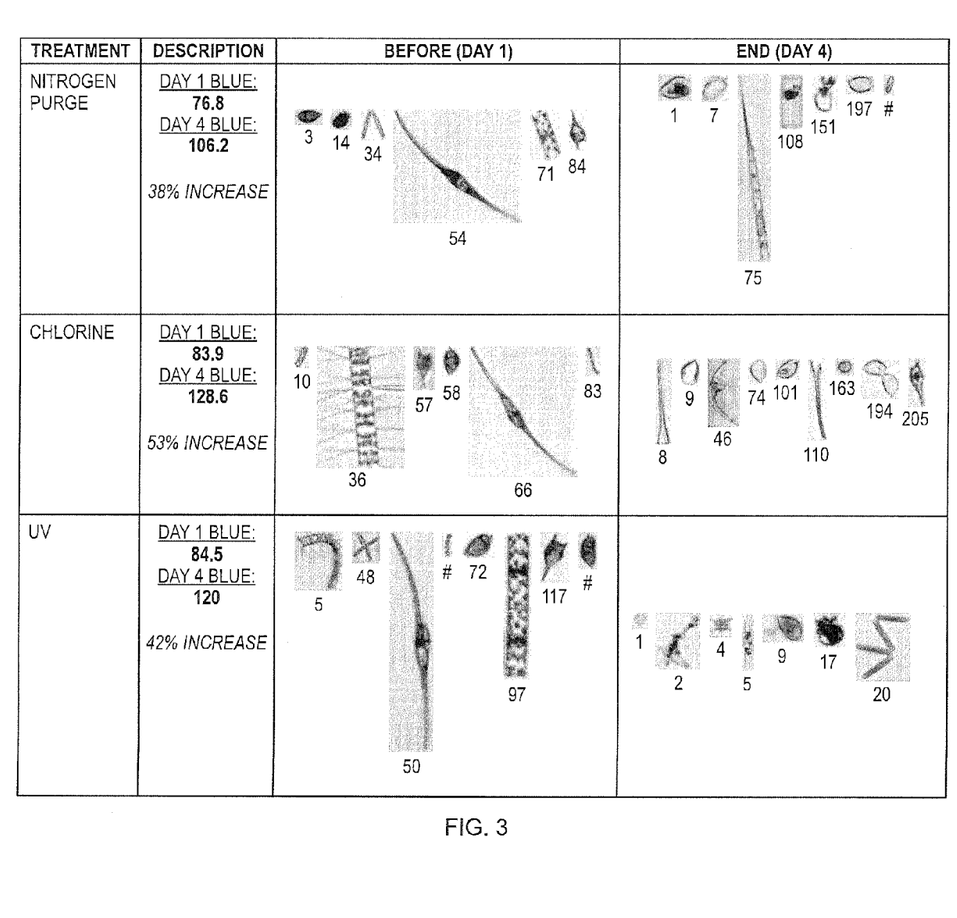
FIG. 3 is a table of treatment type and results and images obtained in a first experiment involving the method of the present invention.
Figure 4:
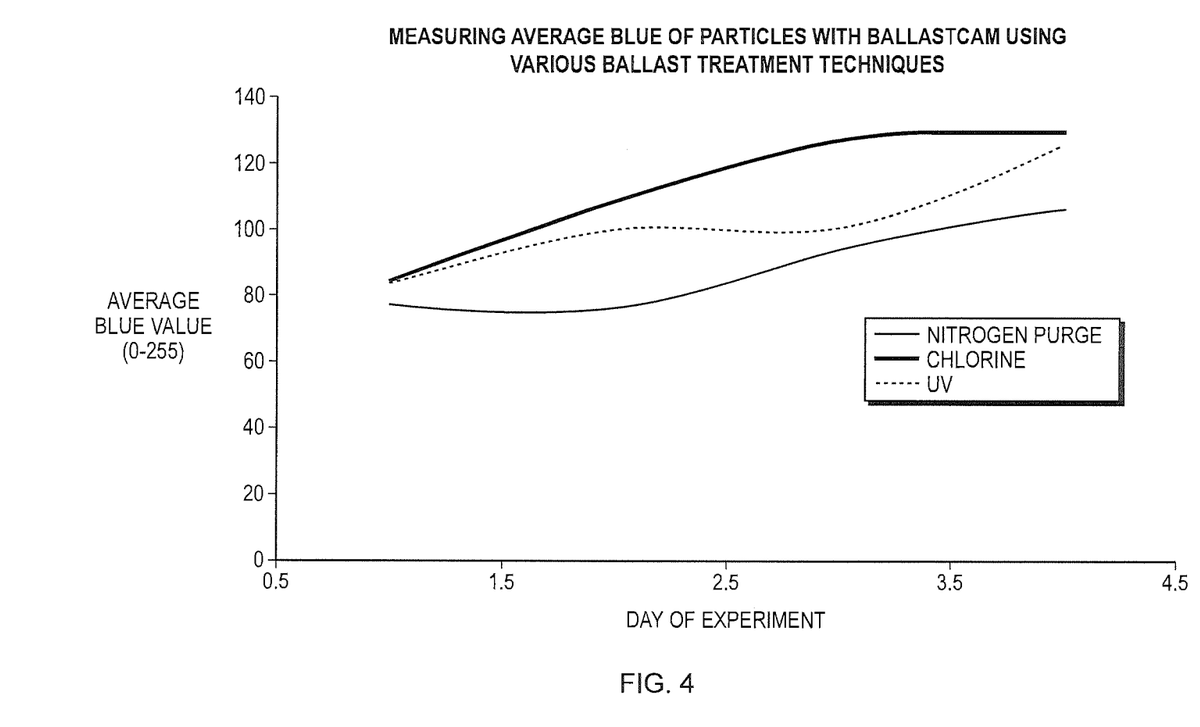
FIG. 4 is a graph showing the average measurement of blue particles detected in the first experiment.

Two experiments were conducted to evaluate the effectiveness of the method of the present invention in providing an assessment of the impact of a fluid treatment procedure. In the first experiment, raw water was drawn from the Portland, Me., area of Casco Bay to serve as a typical ballast water sample. The sample was thoroughly mixed and separated into 1 Liter bottles. Each bottle represented a different ballast water treatment technique: Nitrogen Purge, Chemical Treatment (Chlorine), and UV exposure. The purpose of the first experiment was to determine whether it was possible to differentiate between when the organisms are live (Start of experiment), and when they are dead (Day 4). Specifically, the steps of the method of the present invention were carried out on Day 1 prior to the treatment process. The steps of the method of the present invention were again carried out four days after treatment for the purpose of evaluating the effectiveness of the treatment. The differentiation was made with respect to the amount of blue color measured using the FlowCam® system, including whether the amount of blue color observed increased as the organisms died due to the transparency of the organism's remains. FIGS. 3 and 4 represent the results of the first experiment. As can be seen from FIGS. 3 and 4, it was determined that it is possible to detect a change in blue color of the organism images captured. In addition, it was also determined that a quantitative distinction could be made among the three methods of treatment employed.

Figure 5:
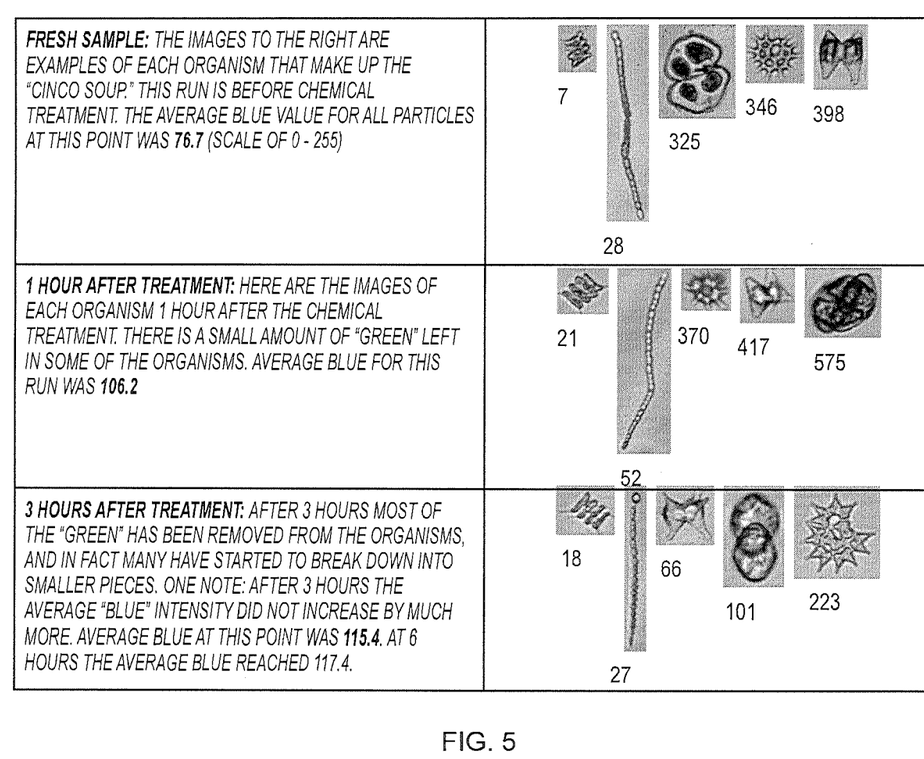
FIG. 5 is a table of treatment type and results and images obtained in a second experiment involving the method of the present invention.
Figure 6:
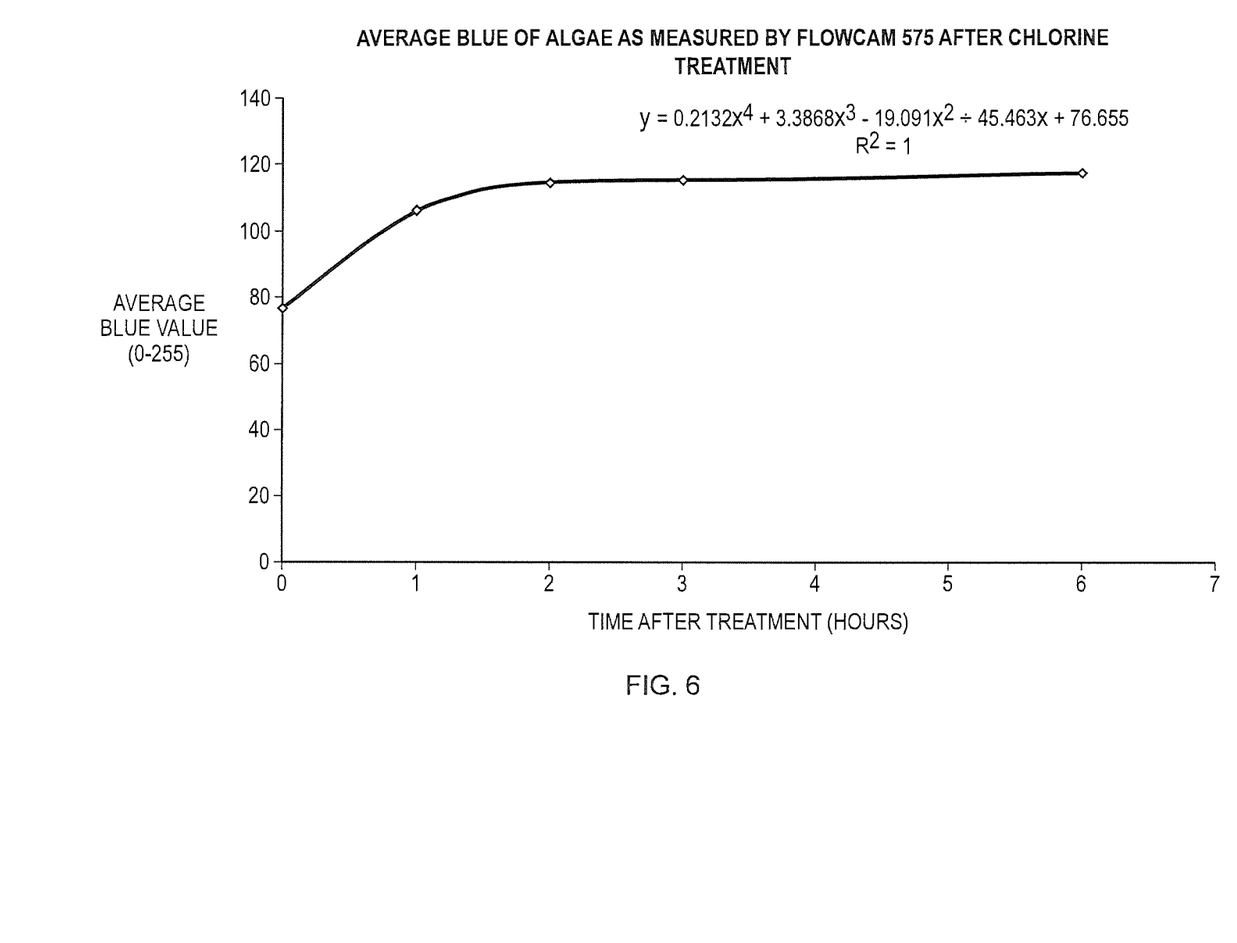
FIG. 6 is a graph showing the average measurement of blue particles detected in the second experiment.

The second experiment was designed to give an indication of what particle parameters determined by the FlowCam® system can be used to indicate how 'dead' a ballast water sample is after undergoing a chemical treatment intended to kill organisms. In the second experiment, 120 ml of a fluid representative of ballast water was set aside in a beaker and then 1 ml of the sample was analyzed with the FlowCam® system in accordance with the steps listed above. Soon after the analysis was completed, approximately 0.25 ml of chlorine bleach was added to the sample resulting in a 0.25% Cl mix (volume/volume). After one hour, the sample was analyzed and the average blue for all the particles was monitored. The analysis was repeated 2 hours, 3 hours, and 6 hours after the treatment was performed. Analysis of the samples for the second experiment was specifically carried out on Flow- Cam® system serial number 575 with a 10× objective, FC100 flow cell, color camera, and in AutoImage mode. FIG. 5 shows the results and images for samples taken before treatment and one and three hours after treatment. It can be seen that qualitative and quantitative determinations have been made indicating the effectiveness of the treatment with chlorine based on the observed blue color of the organisms detected. FIG. 6 also corresponding information, including that the treatment was substantially completed after about two hours, with little further indication of increasing blue color observed.

There is a noticeable effect of before-and-after chemical treatment of fluid samples containing organisms as measured by a version of the system 10 using the method of blue color observation of the present invention. It will be understood that various modifications may be made without departing from the spirit and scope of the invention. For example, the system may be used to detect any particle change indicative of organism death. While the invention has been described with respect to a particle organism that presents blue when dead, other changes are detectable with the system and method of the present invention including, but not limited to, a change to a different color, such as green or red, or a change from opaque to transparent. Accordingly, other embodiments are within the scope of the claims appended hereto.

What is claimed is:

1. A method for determining the effectiveness of a fluid treatment process, the method comprising the steps of:

a. acquiring a first sample of a fluid to be treated prior to treatment;

b. analyzing the first sample with particle imaging for particles in the first sample, including obtaining color images of the particles in the first sample;

c. acquiring a second sample of the fluid after the fluid has been treated;

d. analyzing the second sample with particle imaging for particles in the second sample, including obtaining color images of the particles in the second sample;

e. defining a particle image color indicative of particle death; and f. comparing the color images of the particles in the first sample with the color images of the particles in the second sample to determine a change in particle image color corresponding to the defined particle image color.

2. The method of claim 1 wherein the defined particle image color is blue and an increase in the color blue in the color images of the particles in the second sample indicates that the treatment has produced the death of particles in the fluid.

3. The method of claim 1 further comprising the step of repeating steps d and f X more times, wherein X≥1.

4. The method of claim 1 wherein the fluid is ballast water.

5. A system for determining the effectiveness of a fluid treatment process, the system comprising:

a. a particle imaging system configured to:

i. acquire a first sample of a fluid to be treated prior to treatment;

ii. acquire a second sample of the fluid after the fluid has been treated;

iii. analyze the first sample for particles, including obtaining color images of the particles in the first sample; and iv. analyze the second sample for particles, including obtaining color images of the particles in the second sample; and b. a computing device including information defining a particle image color indicative of particle death, wherein the computing device is configured to compare color images of the particles in the first sample with the color images of the particles in the second sample and determine a change in particle image color corresponding to the defined particle image color.

* * * * *